United States Patent [19]

Fujiwhara et al.

[11] 4,063,950
[45] Dec. 20, 1977

[54] DIR COUPLER THAT FORMS COLORLESS REACTION PRODUCT

[75] Inventors: Mitsuto Fujiwhara; Takaya Endo; Shoji Kikuchi; Ryosuke Satoh, all of Hino, Japan

[73] Assignee: Konishiroku Photo Industry Co., Ltd., Tokyo, Japan

[21] Appl. No.: 589,396

[22] Filed: June 23, 1975

[30] Foreign Application Priority Data

July 6, 1974 Japan .................................. 49-77510

[51] Int. Cl.$^2$ .......................... G03C 5/30; G03C 7/00; G03C 1/06; G03C 1/48
[52] U.S. Cl. .......................................... 96/66.3; 96/3; 96/29 D; 96/55; 96/95
[58] Field of Search ................. 96/3, 29 D, 9, 5, 66.3, 96/95, 76 R, 55

[56] References Cited

U.S. PATENT DOCUMENTS

| | | | |
|---|---|---|---|
| 3,028,238 | 4/1962 | Puschel et al. | 96/9 |
| 3,227,554 | 1/1966 | Barr et al. | 96/3 |
| 3,580,722 | 5/1971 | Sakamoto et al. | 96/100 |
| 3,632,345 | 1/1972 | Marx et al. | 96/95 |
| 3,928,041 | 12/1975 | Fujiwhara et al. | 96/3 |
| 3,932,185 | 1/1976 | Matsuura | 96/76 R |
| 3,938,996 | 2/1976 | Fujiwhara et al. | 96/95 |
| 3,958,993 | 5/1976 | Fujiwhara et al. | 96/95 |
| 3,961,959 | 6/1976 | Fujiwhara et al. | 96/95 |

*Primary Examiner*—David Klein
*Assistant Examiner*—Richard L. Schilling
*Attorney, Agent, or Firm*—Flynn & Frishauf

[57] ABSTRACT

A light-sensitive silver halide photographic material comprising a new development inhibitor releasing type compound and a process for developing thereof.

14 Claims, No Drawings

DIR COUPLER THAT FORMS COLORLESS REACTION PRODUCT

This invention relates to a light-sensitive silver halide photographic material which comprises a novel development inhibitor releasing type compound and a process for developing the said material. Especially, this invention relates to a light-sensitive silver halide photographic material and a process for developing thereof which comprises a compound having the following formula:

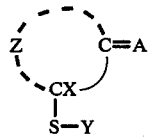

wherein A represents an oxygen atom or a = $NR_1$ radical in which $R_1$ is a hydroxyl or an amino radical that may be substituted, Z represents a non-metallic atomic group necessary to complete an alicyclic or a heterocyclic ring, both of which may be substituted, saturated or unsaturated, X represents a halogen atom,

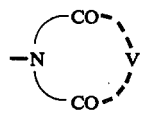

or -S-Y in which W represents an alkyl, aryl, heterocyclic ring, acyl or —$SO_2R_2$ radical wherein $R_2$ represents an alkyl, aryl or a heterocyclic ring radical, and V represents a non-metallic atomic group necessary to complete a heterocyclic ring containing a nitrogen atom and Y represents a radical capable of forming a compound having development inhibiting action together with a sulfur atom when the bond of the thioether is split.

Heretofore, there has been known the fact that a compound releasing development inhibitor according to the density of the image on development (hereinafter this compound is referred to as development inhibitor releasing type compound) is in advance incorporated into light-sensitive photographic material. This compound is a type of compound which reacts with an oxidation product of a colour developing principal agent and releases a development inhibitor. As representative compounds there have been known the so-called DIR couplers which have radicals capable of forming development inhibitors in the active center of couplers when the radicals are released from the active center. These DIR couplers form dyes when these couplers couple with oxidation products of the colour developing principal agents and have the character of release development inhibitors.

The development inhibitor releasing type compounds are generally used for the following object. That is, the development inhibitor releasing type compounds are characterized in that they release development inhibitors according to the density of the image on development and the released development inhibitors are expected to have the following two image effects: the so-called intra-image effect such as elevates the control of the image tone, granulation of the image, sharpness of the image when they are released into the emulsion layer, and the so-called inter-image effect such as elevate the so-called masking action for inhibiting development of other layers according to the density of the image of the layer of the diffusion origin in the light-sensitive colour photographic materials when the development inhibitors are diffused into other layers and the colour tone based on development inhibiting action of other layers in the case of monochromatic exposure.

But the development inhibitor releasing type compounds which have been so far known are not satisfactory for the above object. For example, the development inhibitor releasing type compounds form dyes when colour-developed. As a result, turbidity of the image can occur when the choice of the dyes is careless or the desired inhibiting effect cannot be obtained when the dyes are not adequately selected or they are quite not suitable for some kinds of light-sensitive photographic materials. Or in the case of not forming dyes when colour-developed, they are poor in reactivity with an oxidation product of a colour developing principal agent so that a large amount of them must be added. Therefore such defects in that photographic characters (for example, sensitivity et al) or durability are deteriorated based on these causes or in that satisfactory results cannot be obtained in the case of a small amount addition of the development inhibitor type compounds are produced.

This invention is to improve such defects by using some type of development inhibitor releasing type compounds and to obtain an excellent image by excellent intra-and inter-image effects.

The development inhibitor releasing type compounds used for this invention are those which form substantially colourless compounds and release development inhibitors by reacting with oxidation products of colour development principal agents and have the following formula:

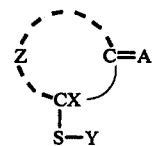

wherein A represents an oxygen atom or =$NR_1$ radical in which $R_1$ represents a hydroxyl or amino radical which may be substituted, Z represents a non-metallic atomic group necessary to complete an alicyclic or heterocyclic ring, both of which may be substituted, saturated or unsaturated, X represents a halogen atom,

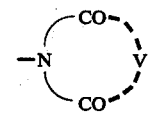

or -S-Y in which W represents alkyl, aryl, heterocyclic ring, acyl or —$SO_2$-$R_2$ radical in which $R_2$ represents an alkyl, aryl or heterocyclic ring radical and V represents a non-metallic atomic group necessary to form a heterocyclic ring containing a nitrogen atom and Y represents a radical capable of forming a compound having development inhibiting action with a sulfur atom when the thioether bond is split.

These compounds form colourless compounds even if they react with oxidation products of colour development principal agents. Therefore, as the compounds thus formed do not constitute a part of the final image, it is unnecessary to use compounds having different structure according to the object for use, for example kinds of layers so that these compounds have an advantage in that a single compound can be used in any layer or any light-sensitive photographic material. Further these compounds have extremely excellent reactivity with oxidation products of colour development principal agents so that they have an advantage in that an excellent intra-and inter-image effect can be obtained by using a small amount of them. According to kinds of the alicyclic or heterocyclic rings or substituents of the compound having the above formula, diffusive or non-diffusive development inhibitor releasing type compounds can be selected so that there is an advantage capable of multiple selection. For example, the diffusive compounds can be incorporated into any layer of constitutional layers of light-sensitive colour photographic material and in the extreme case, they can be incorporated into only one layer so as to react for all layers and according to diffusivity, it is possible to react with each of layers stepwise depending upon the situation of this one layer. Also, for example, the diffusive compounds can be incorporated into a colour developer. On the other hand, the non-diffusive compounds can be used for providing intra-and inter-image effect for only a definite layer. For example, they can be used so as to make variation of density of each layer in case where a stepwise variation between each layer is given.

As representative compounds having the above formula, A in the formula represents an oxygen atom or $=NR_1$ radical in which $R_1$ is a hydroxyl radical or an amino radical which may substituted and especially when A is $=NR_1$, $R_1$ in $=C=N-R_1$ formed as the result of dehydrating reaction between a carbonyl reagent having the formula of $H_2N-R_1$ and a ketone radical is representative. As representative compounds of $H_2N-R_1$, there can be mentioned, for example, hydroxylamine, hydrazine, semicarbazide, thiosemicarbazide and the like. As exemplified hydrazines there can be mentioned hydrazine, phenylhydrazine or phenylhydrazine substituted with an aryl, alkoxyl, carboalkoxyl radical or halogen atom, and isonicotinicacid hydrazide. Also as semicarbazides, there can be mentioned phenylsemicarbazide, or phenylsemicarbazide substituted with an alkyl, alkoxyl, carboalkoxyl radical or halogen atom. As thiosemicarbazide, there can be mentioned several derivatives like those in semicarbazides. Also, as Z in the above formula, Z represents a 5-, 6- or 7- membered alicyclic ring or heterocyclic ring containing nitrogen, oxygen or sulfur atom both of which rings may be saturated, unsaturated or substituted and as exemplified examples of Z, for example, cyclopentanone, cyclohexanone, cyclohexadione, cyclohexenone piperidone (for example, 2-, 3-, 4- piperidone), lactone (for example, 4-~7-membered ring), pyrrolidone, hydantoin and the like are representative. These alicyclic and heterocyclic ring may contain more than one substituent such as alkyl, aryl, alkoxyl, aryloxy, acyl alkoxycarbonyl radicals, or halogen, nitrile, nitro, sulfonamido or acylamino or may form a condensed ring at suitable place (for example, indanone, benzocyclohexenone, benzocycloheptenone, oxyindole). Also, these alicyclic or heterocyclic rings may contain more than one —S-Y radical (wherein Y has the same meaning as above) at the carbon atom next the carbonyl radical. X in the formula represents halogen atoms such as fluorine, chlorine and bromine and —O-W wherein W is preferred to be an alkyl radical having 1~5 carbon atoms or aryl or a heterocyclic ring such as substituted or unsubstituted benzene, pyridine, furan, or thiophene. When W is an acyl radical, that is, —$COR_3$, $R_3$ is preferred to be an aryl or alkyl radical. When W is —$SO_2$-$R_2$, -$R_2$ is preferred to be an alkyl, aryl radical and further heterocyclic rings such as pyridine, furan, thiophene, piperidine, pyrrolidone, and morpholine. Also, X may be

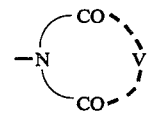

wherein as the representative heterocyclic ring containing nitrogen formed with V, there can be mentioned succinimide, phthalimide, hydantoin, urazol and their derivatives. On the other hand, Y in the formula is a radical forming a compound having development inhibiting action such as an allylmercapto compound, mercapto heterocyclic compound, thioglycollicacid type compound, cysteine or glutathione with sulphur atom when the thioether bond is split and the sulfur atom is detached. As representative mercapto compounds of Y, there can be mentioned heterocyclic mercapto compounds such as mercaptotetrazole type compound, especially 1-phenyl-2-mercaptotetrazole, 1-nitrophenyl-5-mercaptotetrazole, 1-naphthyl-5-mercaptotetrazole, mercaptothiazole compounds, especially 2-mercaptobenzthiazole, mercaptonaphthothiazole, or mercaptooxadiazole compounds, mercaptopiperidine compounds, mercaptothiadiazole compounds, especially 2-mercaptothiadiazolotriazine or mercaptotriazine compounds, mercaptotriazole compounds, mercaptobenzene compounds, especially 1-mercapto-2-benzoic acid, 1-mercapto-2-nitrobenzene, 1-mercapto-3-heptadecanoylaminbenzene. As exemplified examples of the compounds having the above formula, there can be mentioned the following compounds:

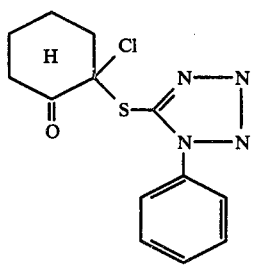

(1)

-continued
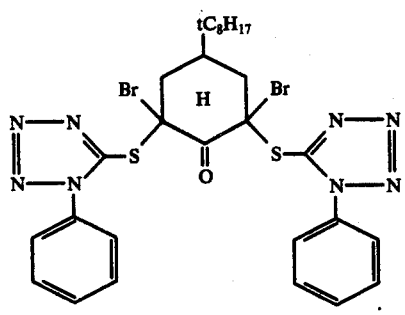
(2)
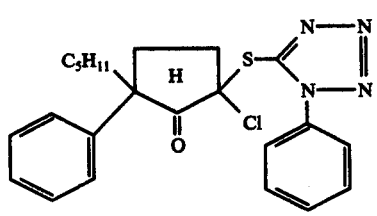
(3)
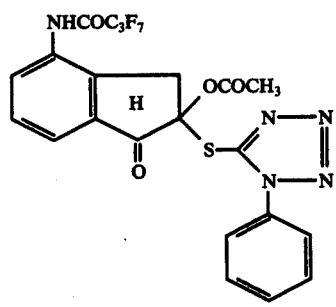
(4)
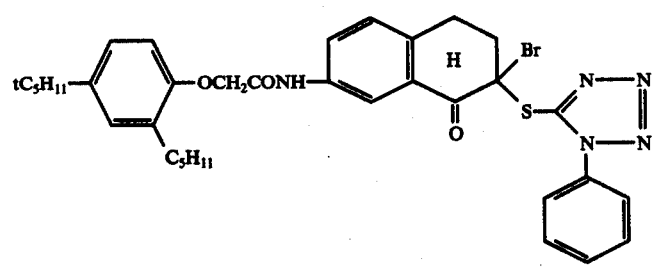
(5)
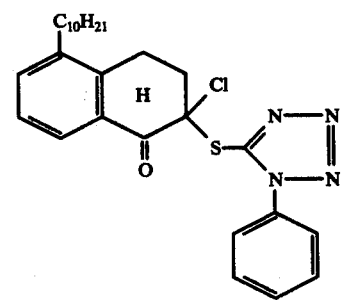
(6)
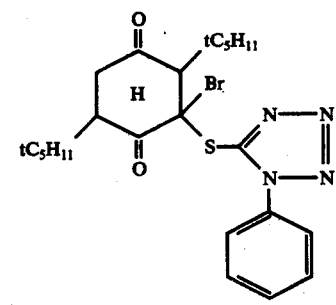
(7)

-continued
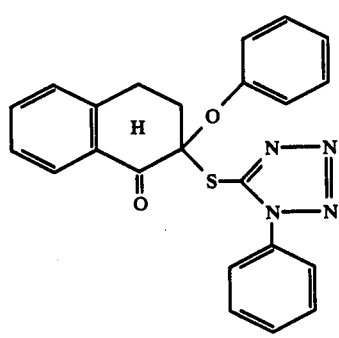
(8)
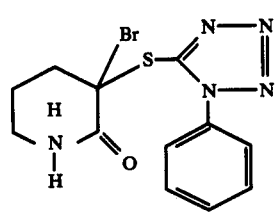
(9)
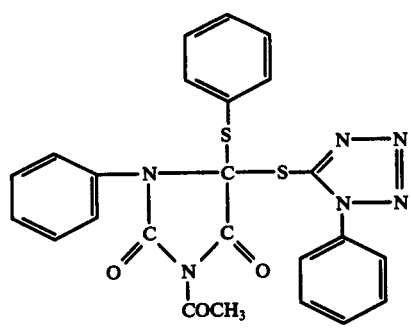
(10)
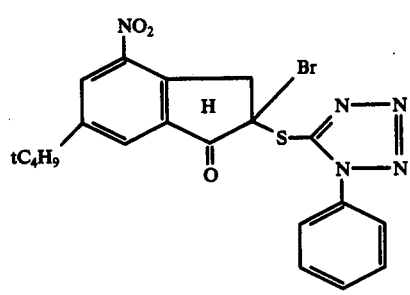
(11)
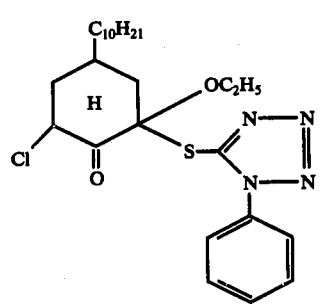
(12)

-continued
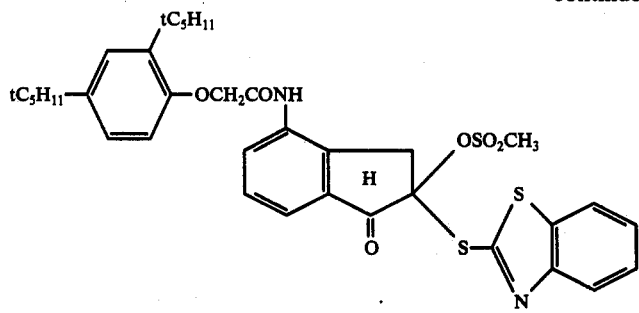 (13)
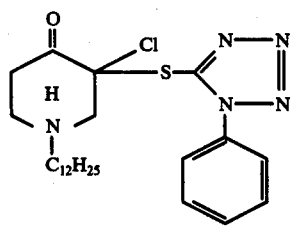 (14)
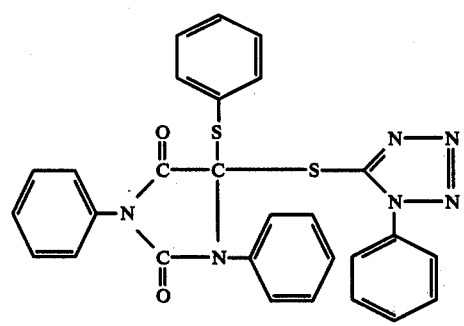 (15)
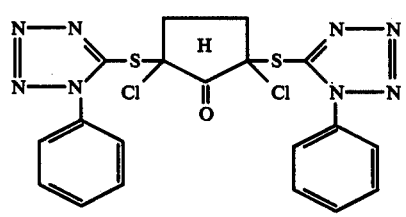 (16)
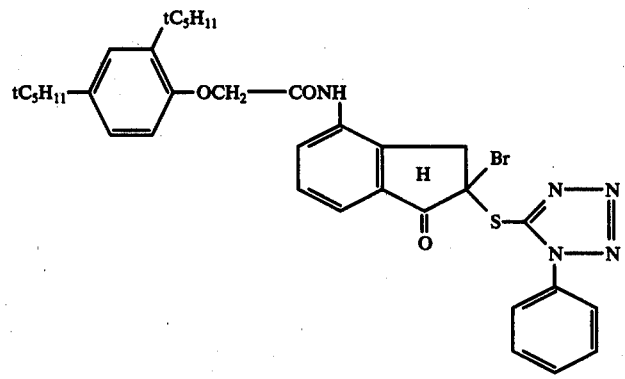 (17)
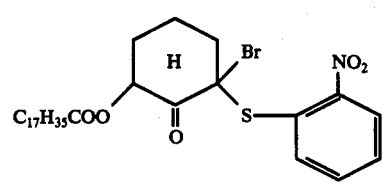 (18)

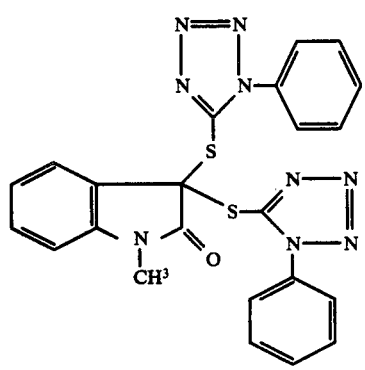
(19)
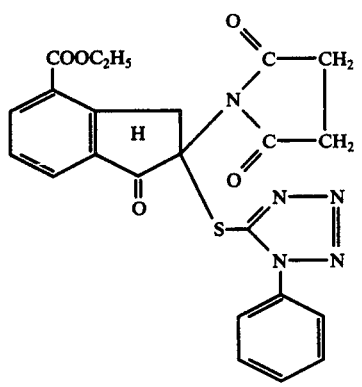
(20)
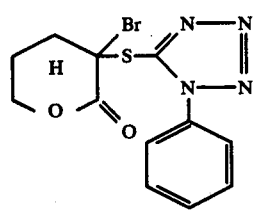
(21)
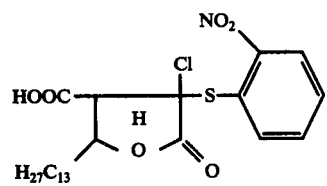
(22)
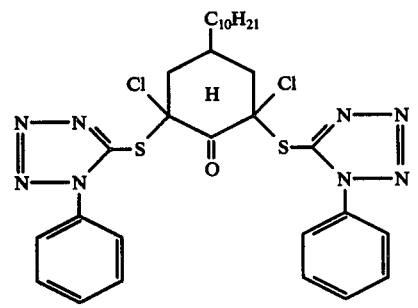
(23)
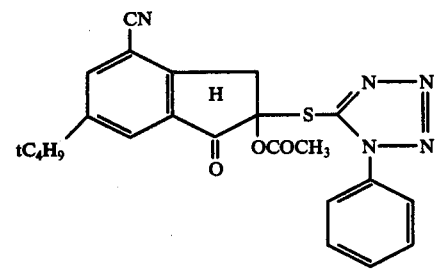
(24)

-continued
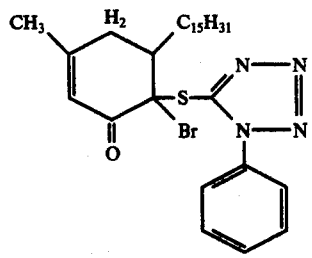
(25)
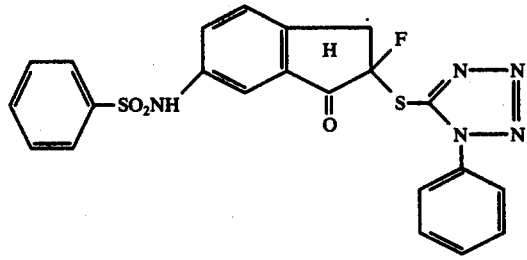
(26)
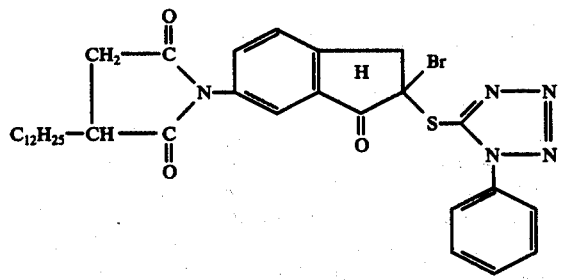
(27)
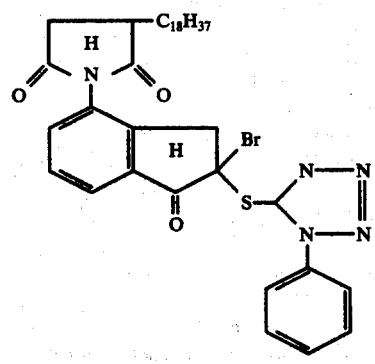
(28)
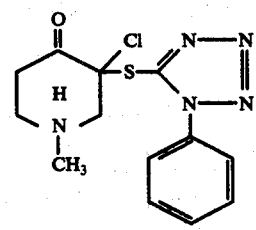
(29)
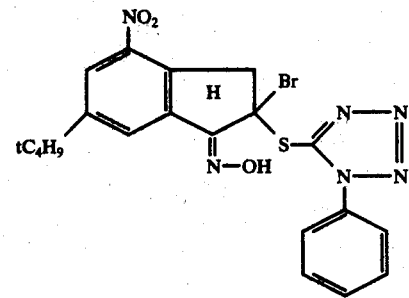
(30)

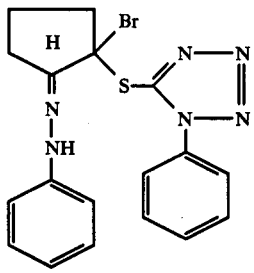

(31)

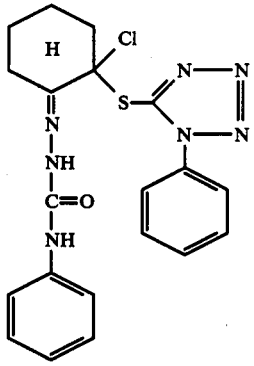

(32)

Next, among the above compounds, synthetic methods for preparing some representative compound will be illustrated as follows, but other compounds can be easily synthesized in the same way. Synthetic example 1: Synthesis of exemplified compound (11)

In 1l of chloroform 48.9g of 2-(1-phenyl-5-tetrazolylthio)-4-nitro-6-tert-butyl-1-indanone was dissolved and 19.2g of bromine was added dropmise to this solution under stirring at room temperature and then the mixture was warmed to 50° C and continued to stir at the same temperature for one hour. Next, the solvent was distilled off under reduced pressure and the residue was recrystallized from a mixture of ethyl acetate and ethyl alcohol to give the object compound having m.p. 180° C.

The exemplified compounds (2), (5), (7), (9), (17), (18), (21), (25), (27) and (28) can be synthesized by the same bromination process as in the above (11). Also, the exemplified compounds (1), (3), (6), (14), (16), (23) and (29) can be synthesized by chorination with sulfuryl chloride instead of bromination with bromine. Further, the exemplified compound (26) can be obtained by reacting the corresponding chloro compound with potassium fluoride. Synthetic Example 2: Synthesis of exemplified (4)

In 1l of acetonitrile 84.4g of 2-bromo-4-perfluorobutanamido-1-indanone and 16.4g of sodium acetate were refluxed under stirring for 2 hours. The solvent was distilled off and the residue was extracted with ethyl acetate and the extract was completely washed with water. The ethyl acetate solution was dried over sodium sulfate and distilled off under reduced pressure. The residue was twice recrystallized from methanol to give 2-acetoxy-4-perfluorobutanamido-1-indanone. Then, 0.1g of 2-acetoxy-4-perfluorobutanamido-1-indanone was dissolved in 500ml of chloroform and a solution of 23.3g of 1-phenyl-5-tetrazolylsulfenyl chloride in 250ml of chloroform was added dropwise under stirring at room temperature over about 2 hours and the mixture was stirred at room temperature for 3 hours. The solvent was distilled off and the residue was twice recrystallized from ethyl alcohol to give the object compound having m.p. 145° – 150° C.

The exemplified compounds (8), (10), (12), (13), (15), (20) and (24) can be obtained in the same way as in the above example by synthesizing the respective parent compounds by reacting the corresponding bromo compounds with sodium compound of the substituents and by reacting the parent compounds with the corresponding sulfenyl chloride. Synthetic example 3: Synthesis of exemplified compound (19)

In 300ml of carbon tetrachloride 14.7g of N-methyloxyindole was dissolved and a solution of 42.3g of 1-phenyl-5-tetrazolylsulfenylchloride in 200ml of carbon tetrachloride was added dropwise under stirring at room temperature over about two hours and then the mixture was stirred further for one hour and the obtained crystals were filtered out. After washing with cooled ethyl alcohol, the crystals were recrystallized from ethyl alcohol to give the object compound having m.p. 178° – 180° C. Synthetic example 4: Synthesis of exemplified compound (30)

In 1l of 95% ethyl alcohol a mixture of 48.8g of exemplified compound (11), 10g of hydroxylamine hydrochloride and 30ml of pyridine was refluxed under heating for 4 hours and the reaction mixture was dissolved in ethyl alcohol under heating and allowed to stand to give the object compound having 135° – 140° C. The exemplified compounds (31) and (32) can be also obtained in the same way as in the above example.

To confirm the structure of the synthesized compounds, elementary analysis of them was effected. But the result of sulfur content of them was tabulated as follows:

| Exemplified compound (No) | Elementary analysis (S) | |
|---|---|---|
| | Calculated(%) | Found(%) |
| (1) | 10.38 | 10.12 |
| (2) | 8.91 | 8.72 |
| (3) | 7.27 | 7.30 |
| (4) | 5.55 | 5.25 |
| (5) | 4.64 | 4.50 |

-continued

| Exemplified compound (No) | Elementary analysis (S) | |
|---|---|---|
| | Calculated(%) | Found(%) |
| (6) | 6.45 | 6.78 |
| (7) | 6.34 | 6.30 |
| (8) | 7.74 | 7.72 |
| (9) | 9.05 | 8.79 |
| (10) | 12.76 | 12.51 |
| (11) | 6.57 | 6.72 |
| (12) | 6.56 | 6.46 |
| (13) | 14.82 | 14.98 |
| (14) | 6.71 | 6.81 |
| (15) | 11.95 | 12.02 |
| (16) | 12.69 | 12.38 |
| (17) | 4.74 | 4.99 |
| (18) | 5.34 | 5.30 |
| (19) | 12.84 | 12.76 |
| (20) | 6.72 | 6.48 |
| (21) | 9.03 | 9.12 |
| (22) | 6.57 | 6.32 |
| (23) | 9.80 | 10.01 |
| (24) | 6.72 | 6.91 |
| (25) | 5.58 | 5.52 |
| (26) | 13.35 | 13.51 |
| (27) | 4.91 | 4.93 |
| (28) | 4.35 | 4.48 |
| (29) | 9.03 | 9.12 |
| (30) | 6.00 | 5.81 |
| (31) | 7.47 | 7.87 |
| (32) | 7.26 | 7.52 |

According to this invention, the compounds having the above formula can be used together with several photographic additives. For example, as hardening agents used in combination with these compounds, there can be mentioned aldehyde type, aziridine type [for example, described in PB Report 19921, U.S. Pat. Nos. 2,950,197, 2,964,404, 2,983,611, and 3,271,175, Japanese patent publication (hereinafter referred to as PP) Sho 46-40898], isoxazole type (for example, described in U.S. Pat. Nos. 3,316,095), epoxy type (for example, described in U.S. Pat. No. 3,047,394, DP 1085663, BP 1033518, PP Sho 48-35495), vinylsulfone type [for example, PB Report 19920, DP 1100942, BP 1251091, Japanese patent application (hereinafter referred to as PA) Sho 45-54236, PA Sho 48-110996 and 115745, U.S. Pat. Nos. 3,539,644 and 3,490,911], acryloyl type (for example, described PA Sho 48-27949, U.S. Pat. No. 3,640,720), carbodiimide type (for example, described in U.S. Pat. No. 2,938,892, PP Sho 46-38715, PA Sho 49-15095), maleimide type (for example, described in U.S. Pat. No. 2,992,109 and .... 3232763), acetylene type (for example described in DP 2130483), methanesulfonate ester type (for example, described in U.S. Pat. Nos. 2,726,162 and 2,816,125), mucohalogenic acid type (for example, described in U.S. Pat. Nos. 3,110,597, PP Sho 48-30948) high polymertype (for example, described in U.S. Pat. No. 3,058,827, BP 822061, 1049083, 1202052 and 1230354), triazine type hardening agents (for example, U.S. Pat. No. 3,288,775, PA Sho 48-108497). Especially, as preferred hardening agents which give the desired effect when used in combination with the compounds having the above formula, there can be mentioned those described in U.S. Pat. No. 2,726,162, PA Sho48-30948, PB Report 19921, PP Sho 46-40898, PA Sho 48-108497, PA Sho 45-54236, and 110996, PA Sho 48-115745, PB Report 19920, PA Sho 48-27949, PA Sho 49-15096, BP 1251091. When the compounds having the above formula are used in combination with these hardening agents, especially light-sensitive silver halide colour photographic materials having better colour purity and granularity and further better hardening characters resistant to high temperature and quick treatment can be obtained.

Also, when these hardening agents are applied to light-sensitive silver halide colour photographic materials, those agents can be added in advance and mixed in the coating solution or mixed continuously in the coating solution just before coating by using apparatus such as is described in U.S. Pat. No. 3,286,992.

In case where the light-sensitive silver halide photographic materials according to this invention are used for forming a coupler image, couplers may be incorporated into the said photographic materials. As useful couplers, there can be mentioned open chain ketomethylene tape yellow couplers, pyrazolone type magenta couplers, phenol or naphtol type cyan couplers and in combination with these couplers, it is possible to use azotype coloured couplers, oxazone type compounds, and development diffusive dye releasing type couplers for automasking. As yellow couplers, there have been now used open chain ketomethylene compounds and as useful yellow couplers there can be mentioned, for example, pivalylacetoanilide type described in FP 1291110, benzoylacetoanilide type described in PP Sho 46-19031, U.S. Pat. No. 2,875,051, and further active center-O-allyl substituted compounds described in U.S. Pat. No. 3,408,194, active center-O-acyl substituted compounds described in U.S. Pat. No. 3,447,928, active center hydantoin substituted compounds described in Japanese open-laid application (hereinafter referred to as OLA) Sho 48-29432, active center urazole substituted compounds described in OLA Sho 48-66834, active center succinimide substituted compounds described in PA Sho 45-119053, active center mono-oxoimide substituted compounds described in PA Sho 48-79309, active center pyridazone substituted compounds described in OLA Sho 49-10736, active center fluorosubstituted compounds described in BP 944490, active center chloro-or bromo-substituted compounds described in BP 780507, active center-O-sulfonyl substituted compound described in BP 1092506, all active center-substituted compounds of which are called so-called two-equivalent couplers. Among these yellow couplers, especially useful couplers are those described in U.S. Pat. No. 3,408,194, OLA Sho 48-29432, PA Sho 48-79309, OLA Sho 48-66834.

As magenta couplers used for this invention, there can be mentioned pyrozolone type, pyrazolotriazole type, pyrazolinobenzimidazole type, and indazolone type compounds. As pyrazolone type magenta couplers, there can be mentioned those described in U.S. Pat. Nos. 3,127,269, 2,600,788, 3,519,429, 3,419,391, and 3,062,653, BP 1142553, DP 2162778, OLA Sho 49-29639, PA Sho 44-8433, as pyrazolotriazole type magenta couplers, those described in DP 1810464, Belg. P 792525, as pyrazolinobenzimidazole type magenta couplers, those described in U.S. Pat. No. 3,061,432, PP Sho 46-60479, DP 2156111, as indazolone type magenta couplers, those described in Belg. P 769116. As especially preferred magenta couplers, there can be mentioned those described in PA Sho 44-8433, and 3-anilinopyrazolone magenta couplers described in U.S. Pat. No. 3,127,269.

As useful cyan couplers used for this invention, there can be mentioned, for example, phenol compounds described in U.S. Pat. Nos. 2,423,730, 2,801,171, and 2,895,826, and Belg. P 779512, active center-O-aryl substituted naphthol compounds described in U.S. Pat. Nos. 2,474,293, and BP 1084480 and phenol or naphthol compounds described in OLP Sho 47-37425, PA Sho 48-57829, and 69866, PA Sho 49-10787, 25388, 16057, and 37160.

As coloured magenta couplers, arylazo substituted or heteroarylazo substituted compound which are substituted at active center of colourless magenta couplers can be used and, for example, those described in U.S. Pat. Nos. 3,005,712, 2,983,608, and 2,801,171, BP 937621 and PA Sho 44-8433 can be used.

As coloured cyan couplers, there can be used active center arylazo substituted compounds described in U.S. Pat. Nos. 3,034,892, and 2,521,908, BP 1255111 and PA Sho 46-55665 and further masking couplers which react with development oxidation products and make the dye flow into the treatment bath and such as are described in PA Sho 48-57829, and 69866, PA Sho 49-16057, 25388, and 37160, and BP 1084480.

As computing couplers, those described in U.S. Pat. No. 2,742,832, for example, citrazinic acid and the like can be used. Also, as weiss couplers, those such as are described in DP 1155676 can be used. In order to incorporate these couplers and the compounds having the above formula into light-sensitive silver halide colour photographic materials, known several arts which have been heretofore applied to couplers can be applied.

For example, the following methods can be used: as described in U.S. Pat. No. 2,322,027, a method of dissolving these compounds into high-boiling point solvent and incorporating them; as described in U.S. Pat. No. 2,801,170, a method of dispersing couplers and high-boiling point solvent separately in fine particles and mixing them. Also in these dispersion method, use of lower-boiling point solvent can be used as a preferred method. In this case, the compounds having the above formula can be used by mixing with couplers and dispersing or dispersing the above compounds and couplers separately. In the case of using lower-boiling point solvent, it is possible to remove the lower-boiling point solvent from the dispersion liquid, as described in U.S. Pat. No. 2,801,171 or PA Sho 44-76273.

Among solvents used for this invention, especially preferred solvents are as follows: dibutyl phthalate, dioctyl phthalate, diisodecyl phthalate, triphenyl phosphate, tricresyl phosphate, diethyl laurylamide, dibutyl laurylamide, benzyl phthalate, monophenyl-P-tert-butylphenylphosphate, phenoxy ethanol, diethylen glycol, monophenyl ether, dimethoxyethyl pthalate, and hexamethylphosphoramide. Further, there can be mentioned high-boiling point solvents unmixible with water such as are described in U.S. Pat. No. 3,779,765, PA Sho 47-130258, and PP Sho 48-29060. As lower-boiling point solvents, there can be mentioned, for example, methyl isobutyl ketone, $\beta$-ethoxyethyl acetate, methoxytriglycol acetate, acetone, methyl acetone, methanol, ethanol, acetonitrile, dioxane, dimethylformamide, dimethyl sulfoxide, ethyl acetate, butyl acetate, isopropyl acetate, butanol, chloroform, cyclohexane, cyclohexanol and fluorinated alcohol. These lower-boiling point solvents can be used instead of high-boiling point solvents and also by mixing with the latter solvents. And further these solvents can be used alone or in combination of two solvents and more.

As another method, in the case of the couplers and the compounds having the above formula, both of which have water soluble radicals, they can be used in a Fischer type method, that is, by dissolving them in an alkoline solution. It is also possible to incorporate them in the same layer by dispersing one of the couplers and the compound having the above formula and by using the Fischer type method for the other.

As silver halides used for the light-sensitive silver halide photographic materials according to this invention, any silver halide such as silver bromide, silver chlorobromide, silver iodobromide, silver chloroiodobromide or silver chloride which is used for usual silver halide photographic emulsions can be used. These silver halides may be rough or fine particles and can be made by any known method. For example, the methods such as are described in OLA Sho 48-65925, PP Sho 46-18103, and 46-7772, U.S. Pat. No. 2,592,250, and 3,276,877, FP 1557289, U.S. Pat. No. 3,317,322, U.S. Pat. Nos. 2,222,264, 3,320,069, 3,271,157, 3,206,313, 3,367,778, 3,447,927, 2,996,382, 2,184,013, 2,541,472, 3,501,307, 2,563,785, 2,456,953, and 2,861,885, BP 723019, FP 1520821, J.Phot.Sci., 12 242 – 251 (1964) can be used. It is also possible to use by mixing the silver halides made by different methods. Also the silver halide emulsions according to this invention are preferred to remove soluble salts from the emulsions but the unremoved emulsions may be used.

As hydrophilic colloids advantageously used for making sensitizing emulsions in the light-sensitive halide colour photographic materials of this invention, there can be used gelatine, colloidal albumin, agar, gum arabic, alginic acid, hydrolyzed cellulose acetate, acrylamide, imidopolyamide, polyvinyl alcohol, hydrolyzed polyvinyl acetate, water-soluble polymer such as are described in BP 523661, DP 2255711, DP 2046682 and U.S. Pat. No. 3,341,332, gelatine derivatives, for example, phenylcarbamylgelatine acylated gelatine, phthalated gelatine such as are described in U.S. Pat. Nos. 2,614,928, and 2,525,753, or graft copolymers of gelatine with a polymerisable monomer having ethylene radical such as acrylic acid, styrene, acrylate ester, metacrylic acid, and metacrylate ester such as are described in U.S. Pat. Nos. 2,548,520, and 2,831,767. These hydrophilic colloids are advantageously used for making photographic material constituent layers, for example, filter layer, protecting layer, intermediate layer and the like.

The silver halide emulsions applied for the light-sensitive silver halide photographic materials of this invention can be sensitized with several kinds of chemical sensitizers.

As sensitizing agents, there can be used active gelatine, sulfur sensitizing agents (sodium thiosulfate, allylthiosemicarbamide, thiourea, allyisothiocyanate), selenium sensitizing agents (N.N-dimethylselenourea, selenourea), reduction sensitizing agents (triethylene tetramine, stannic chloride), noble metal sensitizing agents, for example, gold sensitizing agents (patassium chloroaurite, patassium aurothiocyanate, patassium chloroaurate, 2-aurosulfobenzothiazole methyl chloride). In the case of using gold sensitizing agents, there can be used ammonium rhodanate as a supplemental agent. Also, palladium, platinum and iridium salt sensitizing agents (ammonium chloropalladate, patassium chloroplatinate and sodium chloropalladate) can be used alone or optionally in combination.

The blue, the green and the red sensitive emulsions can be sensitized optically by using suitable sensitizing dyes in order to give sensitivity for any desired sensitive wave length range to the emulsions. As sensitizing dyes, several kinds of sensitizing dyes can be used alone or in combination of two or more. As sensitizing dyes which are preferably used for this invention, there can be mentioned, for example, methine dyes and styryl dyes such as cyanine, merocyanine, hemicyanine, rhodacyanine, oxonole, and hemioxonole dye. Further, sensitizing dyes such as are described in the following patents or literatures are mentioned to be concretely effective: U.S. Pat. Nos. 1,846,301, 1,846,302, 1,939,201, 1,990,507, 2,072,908, 1,990,507, 2,072,908, 2,112,140, 2,165,338, 2,213,995, 2,269,234, 2,270,378, 2,442,710, 2,454,629, 2,493,748, 2,503,776, 2,519,001, 2,666,761, 2,739,149, 2,739,964, and 2,945,763, BP 424559, 438420, 450958and 505979, DP 929080, and 2049967, PP Sho 43-10251, 10252 and 13821, PP Sho 44-32753, PP Sho 45-27672, 27673, 27674, and 27675, PP Sho 46-18106, and 18108, PP Sho 47-8741, 23573, and 37443, OLA Sho 48-78930, K. E. Mees and T. H. James: Theory of photographic process (3rd Edition, 1966) and Hahmer: Cyanine dyes and related compounds (1964).

Among these patents and literatures, the sensitizing dyes described in the following patents are especially effective for this invention: U.S. Pat. Nos. 2,213,995, 2,503,776, and 2,945,763, DP 929080, and 2049967, PP Sho 43-13821, PP Sho 44-32753, PP Sho 46-18108, PP Sho 47-8741 and 37443 and OLA Sho 48-78930.

In the sensitive silver halide colour photographic materials according to this invention, there can be incorporated following additives as usual several photographic additives into silver halide emulsion layer or its supplemental layer: gamma controler, development accelartor, stabilizer, ultraviolet ray absorber, latent image stabilizer, formaline resistance accelator, image stabilizer, pluorescent brightning agent, anstiycysteine agent, lubricant, metal ion chelating agent, surface active agent, mordant, antistatic agent, agent for preventing colour turbity, viscosity increasing agent, gelatin plasticizer, latex, matting agent and the like.

As gamma controlers, metals belonging to 8th group (for example, rhodium, and ruthenium) or cadmium and thorium can be used. As development accelerators, benzylalcohol and polyoxymethylene type compounds can be used and these compounds can be effective when added in the treating bath. As stabilizers, those compounds which are described in U.S. Pat. Nos. 2444607, 2716062, and 3512982, DP 1189380, 2058626, and 2118411 PP Sho 43-4133, U.S. Pat. No. 3,342,596, PP Sho 47-4417, DP-2149789, PP Sho 39-2825, PA Sho 45-777072. As especially preferred compounds, there can be mentioned 5,6-trimethylene-7-hydroxy-s-triazolo (1,5-a) pyrimidine, 5,6-tetramethylene-7-hydroxy-s-triazolo (1,5-a) pyrimidine, 5-methyl-7-hydroxy-s-triazolo (1,5-a) pyrimidine, 7-hydroxy-s-triazolo (1,5-a) pyrimidine, 5-methyl-6-bromo-7-hydroxy-s-triazolo (1,5-a) pyrimidine, gallic acid ester (for example, isoamyl gallate, dodecyl gallate, propyl gallate, sodium gallate), mercaptans (1-phenyl-5-mercaptotetrazole, 2-mercaptobenzothiazole), benztriazoles (5-bromobenztriazole, 4-methylbenztriazole) benzimidazoles (6-nitrobenzimidazole). As ultraviolet ray absorbers, those compounds which are described in PP Sho 48-763, 5496, 41572, 30492 and 31255, U.S. Pat. No. 3,253,921 and BP 309349 can be used. Among these compounds, ultraviolet ray absorbers such as Tinuvin PS 200, Tinuvin 320 ®, Tinuvin 326 ®, Tunivin 327 ®, Tinuvin 328 ® manufactured by Ciba & Geigy Company Ltd. can be used effectively alone or in combination of them. As latent image stabilizers, aminoacid compounds containing sulfur such are described in DP 2217153 and 2217895 and heterocyclic compounds containing nitrogen such as are described in OLA Sho 49-14120 and 29835 can be used. As formalin resistance accelerators, those compounds which are described in Belg. P 801533,PA Sho 48-134036, PA Sho 46-34675 can be used. Among these compounds, a combination of vinyl-sulfone type hardening agent and non-cyclic urea derivative which are described in Belg. P 801533 and PA Sho 48-134036 are effective.

As image stabilizers, there can be used chroman type compounds described in U.S. Pat. No. 3,432,300, chroman and coumaran type compounds described in U.S. Pat. No. 3,574,627, bisphenol type compounds described in PP Sho 48-31256 and 31625 and phosphorous acid ester type compounds described in PP Sho 48-32728. Among these compounds, those described in PP Sho 48-31256 and 31625 are effective, for example, 6,6'-butylidene bis(2-tert-butyl-4-methylphenol), 4,4'-methylenbis(2.6-di-tert-butylphenol), 2,2'-dimethyl-4,4'-dihydroxy-5,5'-tert-butyl-diphenylsulfide can be mentioned. As fluorescent brightening agents, for example, those compounds which are described in PP Sho 34-7127 can be used. As anticysteine agents, those compounds described in U.S. Pat. Nos. 2732300, 3700453, 2360210 and 2728659 can be used. Among them, those compounds described in U.S. Pat. No. 2732300 and 2360210, for example, 2-methyl-5-hexadecyl-hydroquinone, 2-methyl-5-sec-octadecyl hydroquinone or their combination use are effective. As lubricants, wax, higher aliphatic acid glyceride and higher aliphatic acid higher alcohol esters (for example, those described in U.S. Pat. No. 3121060) can be used. As metal ion chelating agents, ethylenediamine tetraacetic acid or those compounds described in DP 1160302, 1170777 and 1187132, U.S. Pat. No. 3,236,652, PA Sho 48-45113 and 52094 can be used. Among them, those described in PA Sho 48-45113 and 52094 are effective. As surface active agents, anionic type, cathionic type, non-ionic type of amphoteric ion type can be used as improving agents of permeability for coating supplemental agents, emulsions or treating liquids or as materials for control of several physical properties of antifoaming agents or photographic materials can be used. For example, those surface active agents which are described in BP 548532 and 1216389, U.S. Pat. No. 3026202 and 3514293, PP Sho 44-26580, PP Sho 43-17922 and 17926, PP Sho 40-376, PP Sho 43-13166, and 43130, OLA Sho 48-20785, OLA Sho 47-18338, PA Sho 47-89630, FP 2025688 and Belg. P. 773459 are effective. Among them, there can be mentioned to be specially preferred: Anionic active agents such as sodium alkyl-sulfosuccinate (for example, sodium di-2-ethylhexylsulfosuccinate or sodium amyldecylsulfosuccinate), sodium alkylbenzenesulfonate (for example, sodium dodecylbenzenesulfonate), sodium alkylnaphthalenesulfonate (for example, sodium triisopropylnaphthalenesulfonate), non-ionic active agents such as saponin, polyethylene glycol, alkylphenoxypolyethylene glycol, alkylphenoxypolyglycidol, sugar aliphatic acid ester, organosiloxane (for example, polone SR manufactured by Shinetsu Chemical Company Ltd.,), L-76 or l-520 manufactured by Union Carbide Company Ltd.,), amphoteric ion active agents such as sodium alkyl-phenoxypolyethyleneglycol sulfonate (for example, sodium p-t-octylphenoxypolyethyleneglycol sulfonate), N-alkyl-N, N-dipolyoxyethylene-N-carboxymethyl-betaine (for example, N-lauryl-N, N-dipolyoxyethylene-N-carboxymethyl betain) or non-ionic, anionic, cationic or betaine type active agents containing fluorinated alkyl radical (for example, FC-134, FC-172 manufactured by 3M Company Ltd.,). These active agents can be used alone or in combination of several compounds such as is described in OLA Sho 48-101118. As mordants, there can be used N-guanylhydrazone type compounds described in U.S. Pat. No. 2882156, DP 2113381, quaternary oniumchloride compounds described in U.S. Pat. Nos. 2548564, and 3444138, BP 786592, PP Sho 43-10254, tertiary amine or quaternary oniumchloride compounds described in U.S. Pat. No. 2675316, BP 1221195, and 1221131. Among them, those compounds described DP 2113381, U.S. Pat. No. 2548564 are effective. As antistatic agents, there can be used those compounds described in PP Sho 46-24159 and 39312, PP Sho 48-43809, PP Sho 49-4853 and 64, PP Sho 47-8742, PP Sho 48-43130, OLA Sho 48-89979, 90391 and 20785, OLA Sho 47-33627, PA Sho 47-115641, U.S. Pat. Nos. 2882157 and 2979535. Among them, those described in OLA Sho 48-89979 and 90391, PP Sho 46-24159, OLA Sho 47-33627, for example, diacetyl cellulose, styrene-perfluoroalkylsodium maleate copolymer, alkali salt of reaction product of styrene-anhydrous maleic anhydride co-polymer and aminobenzenesulfonic acid, addition product of p-xylidenedichloride and N,N,N',N'-tetramethyltrimethylenediamine are effective.

As agents for preventing colour turbidity (bad desilverization inhibitors) there can be used polymer containing vinyl-pyrrolidine monomer (for example, those described in BP 1052487), polymer containing vinyl oxazolidinone monomer (for example, those described in BP 1070688), polymer containing vinyl imidazole monomer (for example, BP 1880976). As matting agents, those described in BP 1221980, for example, methyl polymetacrylate, polystyrene, alkali soluble polymer, for example, metacrylic acid - methyl metacrylate co-polymer are effective. Further, the use of colloidal silicon oxide is possible.

As latex incorporated in order to improve film physical properties, there can be used copolymer of acrylate ester, or vinyl ester and monomer having other ethylene radical such are described in U.S. Pat. No. 2956884, FP 1395544 and PP Sho 48-43125. As gelatin plasticizers, there can be used glycerol or compounds described in U.S. Pat. No. 2960404, PP Sho 43-4939, PP Sho 45-15462, OLA Sho 48-63715, DP 1904604, and Belg. P 762833. As viscosity increasing agents, there can be used styrene-sodium maleate copolymer, alkylethylenevinylmaleic acid copolymer and those compounds described in U.S. Pat. No. 3767410, Belg. P 558143.

The light-sensitive silver halide colour photographic materials can be provided with supplemental layers such as a filter layer, antihalation layer and irradiation layer and in these layers dyes which are flown out of photographic materials by means of development treatment or bleached can be caused to incorporate. As representative dyes of this kind can be used dyes such as cyanine, merocyanine, styryl, benzylidene, cinamylidene, oxanol, azo, anthraquinone, and triphenylmethane dye.

As dyes used effectively for this invention, there can be mentioned those dyes such as are described in U.S. Pat. Nos. 1884035, 2150695, 2172262, 2241239, 2298731, 2298733, 2322006, 2527583, 2011696, 2622082, 2091579, 2739888, 2865752, 2956879, and 3247127, PP Sho 28-5731, PP Sho 31-5920, and 10578, PP Sho 39-22069, PP Sho 43-13168, BP 396646, 446583, 506385, 515998, 646125, and 1128113. Among them, those compounds described in U.S. Pat. Nos. 1884035, 2865752, and 2956879, PP Sho 39-22069, PP Sho 43-13168 and BP 506385 are especially effective.

The light-sensitive silver halide photographic materials can be prepared by coating the silver halide emulsion layers containing the several photographic additives as described above and other constituent layers on supports, if necessary. As supports used to be preferred, there are, for example, baryta paper, paper with polyethylene, polypropylene synthetic paper, glass plate, cellulose acetate, cellulose nitrate, polyvinyl acetal, polypropylene, polyester film such as polyethylene terephthalate, polyamide film, polycarbonate film, and polystyrene. These supports can be adequately chosen according to the use objects of the light-sensitive silver halide photographic materials.

The supports can be, if necessary, under-coated. As representative under-coating materials, there can be mentioned a copolymer of vinyl chloride or vinylidene chloride, copolymer of ester of vinylalcohol, copolymer of acrylic acid or metacrylate esters, copolymer containing unsaturated carboxylic acid, copolymer of dienes such as butadiene, copolymer of acetals, copolymer of unsaturated carboxylic anhydrides such as maleic anhydride, especially vinylalcohol esters such as vinyl acetate or copolymer of styrene or compounds thereof ring-opened with water, alcohols or amines, cellulose derivatives such as nitrocellulose, diacetyl cellulose, compounds containing epoxy radicals, gelatine or deformed gelatine and polyolefin copolymer. These compounds are described in PP Sho 48-14434, PP Sho 47-12433, PP Sho 48-9965, 3564, and 14185, PP Sho 47-35458 and 35459, OLA Sho 47-37921, and 14274, OLA Sho 48-24723, 93672, and 89979. These undercoating materials can be used alone or, if necessary, in combination of them. As described in PP Sho 48-43122, and 24270, OLA Sho 48-26124, these materials can be mixed with gelatine or polyols. Further, mono or polyphenols and its chloro-substituted compounds, cross linking agents (hardening agents) and metal oxides can be used (for example, OLA Sho 48-23862, OLA Sho 48-592). In the case of under-coating of the above materials, they may be used alone, but a method of undercoating successively with a layer comprising the above materials, a mixed layer of gelatine and the above materials and a gelatine layer or a method of under-coating one of the former two layers and a gelatine layer can be effected and, if necessary, multilayer coating can be effected by increasing layers and any method can be adopted according to the object. Also, as described in OLA Sho 48-89731, 85126 and 93672, OLA Sho 47-19824, the treatments such as corona discharge, glow discharge, other electric impact, fire flame treatment, surface roughing and ultraviolet ray irradiation can be applied on the support surface alone or in combination. Further these surface treatments can be applied together with the above material treatments.

The light-sensitive silver halide photographic materials can be colour-developed by means of a usual colour development process after exposure. In the case of reversal process, they are developed with white and black negative developer and then exposed to white ray or developed with a bath containing a nucleating agent and then colour developed with an alkaline developer containing a colour developing agent.

The treatment processes are not limited and any treatment process can be applied. As representative processes, there can be applied, for example, a process such as is described in U.S. Pat. No. 3582322 which comprising, after colour development, combined bleaching and fixing and, if necessary, washing with water and stabilizing and a process such as is described in UST 910002 which comprising, after colour development, bleaching and fixing separately and, if necessary, washing with water and stabilizing.

There is also known a process for treating lower silver content photographic material by means of amplifying agent such as hydrogen peroxide or cobalt complex and such a process can be applied. Also, in the case of treating with such a process, there are a case at which the treatment is effected at higher temperature and a case of treatment at room temperature or in especial case below lower temperature than room temperature.

In the case of high temperature treatment, the prehardening treatment such as is described in U.S. Pat. No. 3342596 can be adopted. Also, according to kinds of treating agent, supplemental baths such as several neuralizing baths are necessary in certain circumstances and, if necessary, these supplemental baths can be optionally used. As processes for practical use of such treatments, there are known Flexcolour chemicals, 3-Chemicals and ME-4 of Eastman Kodak Company Ltd. This invention exhibits enough effect with these treatments, but also does too even if these treatment are changed or amended.

There can be adopted several methods of transferring light-sensitive materials and accordingly there can be used several treatment processors such as machine lift and drain processor continuous sinuosidalpass processor, roler transport processor and belt transport processor.

As special system such as is described in PP Sho 35-1885, PP Sho 36-16989, U.S. Pat. No. 3,189,452, PP Sho 46-40908 and U.S. Pat. No. 3607277, a process which comprising, without dipping the light-sensitive materials into treating bath, coating or spraying the treating liquid on the light-sensitive material is effective for treating the light-sensitive silver halide photographic materials of this invention.

Also, there are developed a method of reproduction for use of treating liquids, and a recovering method of medicals which are important polutionally or in sources and these apparatuses are optionally provided with these treatment apparatuses and the photographic materials are optionally treated by these apparatuses. The treating agents for use are not limited and usual agents can be used and as developing principal agents there are mentioned as follows:

3-Acetamido-4-amino-N, N-diethylaniline,
p-Amino-N-ethyl-N-($\beta$-hydroxyethyl)aniline sulfate,
N,N-diethyl-p-phenylenediamine,
2-Amino-5-diethylaminotoluene,
N-ethyl-N-($\beta$-methanesulfonamidoethyl)-3-methyl-4-aminoaniline,
4-Amino-3-methyl-N-ethyl-N-$\beta$-ethoxyethylaniline,
4-Amino-N-ethyl-3-methyl-N-($\beta$-sulfoethyl)aniline,
4-Amino-N,N-diethylaniline hydrochloride,
4-Amino-3-methyl-N,N-diethylaniline hydrochloride,
4-Amino-3-methyl-N-ethyl-N-$\beta$-(methanesulfonamido)-ethylaniline sulphate hydrate,
4-Amino-3-methyl-N-ethyl-N-$\beta$-hydroxyethylaniline sulfate,
4-Amino-3-dimethylamino-N,N-diethylaniline sulfate hydrate,
4-Amino-3-methoxy-N-ethyl-N-$\beta$-hydroxyethylaniline hydrochloride,
4-Amino-3-$\beta$-(methanesulfonamido)ethyl-N,N-diethylaniline dihydrochloride,
4-Amino-N-ethyl-N-(2-methoxyethyl)-m-toluidine-di-p-toluene sulfonate.

Especially useful developing agents are described in, for example, OLA Sho 48-64932, J. Am. Chem. Soc., 73 3100 - 3125 (1951), K. E. Mees and T. H. James: Theory of Photographic Processes, 3rd Ed., 278 - 311 (1966).

As bleaching agents, there can be used bichromate, hexacyanoferrate, permanganate, ferrichloride, halogen, persulphuric acid, hydrogen peroxide or polyaminocarboxylic acid, for example, iron complex of EDTA (ethylenediaminetetraacetic acid), trichloroacetic acid iron salt or tartaric acid iron salt such as are described in DP 866605, cobalt salt such as is described in DP 954475, BP 777635. Also there can be used those compounds described in U.S. Pat. Nos. 2507183 and 2529981 as bleaching agents of quinone type, those described in USP 2705201 as nitroso compounds, those described in BP 774194, PP Sho 35-1478, BP 1032024 as copper complex salts, those described in USP No. 3264107, PP Sho 41-11068 as halogeno-acid type compounds and these bleaching compounds can be effectively used. There can be used known fixing agents such as thiosulfate salt, thiocyanic salt, for example, thioetherpolycarboxylic acid such as described in USP 2748000, bissulfonylalkane type compound such as in described in OLA Sho 47-330.

Several accelerators of other bleaching or fixing agents can be used effectively. These accelerators can be used especially in bleach-fixing bath in many cases. As representative compounds, there can be used polyethylene oxide type, thiourea type, mercapto type, amine type, onium type and selenium type. For example, those described in BP 746567, PP Sho 45-8506, BP 1138842, PP Sho 45-8836, PP Sho 46-556, DP 2139401, OLA Sho 46-280, OLA Sho 47-7324, and 7325 are especially effective.

In the case of preparing practical treating liquids using these chemicals there can be used several supplemental chemicals, for example, phosphoric acid, acetic acid, citric acid, tartaric acid, boric acid and alkali metal salt or ammonium salt. And antioxidants, development accelerator can be usually incorporated into developers. According to this invention the treatments using these chemicals can be used effectively.

In the light-sensitive silver halide photographic materials according to this invention, the amount of the compound having the above formula used varies with the applied principal object, that is, inter-image effect or intra-image effect or with the kinds of emulsions or compounds used, but an amount of 0.1 -10g per/kg of emulsion is preferred and a remarkable great image effect can be obtained even if the compound is used in a smaller amount in comparison with known development inhibitor releasing type compounds.

Then, this invention will be illustrated in detail by the following examples but they are not meant to limit the scope of this invention.

EXAMPLE 1

Samples I and II were prepared as followed.
Sample I

In 30ml of ethyl acetate and 15ml of buthy phthalate 1.0g of exemplified compound (11) and 15g of magenta coupler -1-(2.4.6-trichlorophenyl)-3-[3-(2.4-di-tert-amylphenoxyacetamido)benzamido]-5-pyrazolone were dissolved and this solution was mixed with 20ml of 10% aqueous solution of Alkanol B manufactured by E.I. du Pont de Nemours & Co. and 200 ml of 5% aqueous solution of gelatine. This mixture was emulsified and dispersed by a collaidal mill. This dispersed liquid was added to 1 kg of green sensitive silver iodobromide emulsion and after dispersion, this dispersed liquid was coated on cellulose triacetate base and dried.

Sample II

As control sample, another sample was prepared in the same way as above except that exemplified compound (11) was not contained.

These samples I and II were exposed through light edge and developed with the colour developer having the following composition and bleached and fixed by means for an usual treatment.

| Composition of the colour developer: | |
| --- | --- |
| N,N-dimethylparaphenylenediamine hydrochloride | 2.0g |
| Anhydrous sodium sulfite | 2.0g |
| Sodium carbonate (monohydrate) | 82.0g |
| Potassium bromide | 2.0g |
| Water to | 1l |

The images consisting of magenta dyes were formed from both of the samples. The sensitivity is the same in both of the samples but $\gamma$ value of the sample II is 0.9 and that of the sample I is 0.6. Further, the magenta image of the sample I consisted of fairly fine particles in comparison with those of the sample II.

EXAMPLE 2

Samples III and IV were prepared as follows:

Sample III

To 1 kg of silver iodobromide emulsion sensitized in red region 15g of 2-[α-2.4-di-tert-amylphenoxy)-butylamido]-4.6-dichloro-5-mephylphenol was added and this emulsion was coated on a cellulose triacetate base. On this red sensitive emulsion layer a green sensitive silver halide emulsion comprising 5g of the compound (17) and 20g of 1-(2.4.6-trichlorophenyl)-3-{3-[α-12.4-di-tert-amylphenoxy)acetamido]benzamido}-5-pyrazolone was coated and dried.

Sample IV

As control sample, Sample IV was prepared in the same as in sample III except that the green sensitive layer contained only the magenta coupler and did not contain the exemplified compound (17).

These samples III and IV were exposed through light edge with red ray and white rays. After that, these samples were developed with the developer used in Example 1 in the same way as in Example 1 and bleached and fixed by means of an usual method.

As results of these experiments, the $\gamma$ values of cyan image of the sample IV obtained by red exposure and white exposure were substantially the same, but the $\gamma$ value of cyan image of the sample III obtained by white exposure was clearly smaller then that obtained by red exposure. This is because the development inhibitor released from the exemplified compound (17) by white ray exposure in Sample III diffused into the under red sensitive layer and as a result prevented the development of the red sensitive layer to cause the $\gamma$ value to decrease.

EXAMPLE 3

The silver iodobromide emulsion which was prepared as follows was coated on a cellulose triacetate base: 0.8g of 1-phenyl-3-(3.5-disulfobenzamido)-4-(n-octadecyloxypheny lazo)-5-pyrozolone disodium salt was stirred in 40ml of water at room temperature and 5cc of 10% sodium hydroxide was add to this solution. Then, this solution was poured into 100ml of 10% gelatine aqueous solution and 8ml of 5% Alkanol B solution and further 16ml of 7% saponine solution was added. The PH of the solution was adjusted to ph 6.8 and 8ml of silver iodobromide emulsion was added thereto. The mixture was stirred for 2 minutes and allowed to stand at 40° C for 30 minutes. After filtration, this solution was coated on cellulose triacetate base.

Then, this layer was exposed to a 40 watt electric lump at a distance of 1.5m for 30 seconds to cause fog. Next, on this emulsion having such fog the emulsion which was prepared as follows was coated:

To a mixture of 0.8ml of 2.4-di-n-amylphenol and 0.8 ml of dimethylformamide, 0.8g of the exemplifed compound (24) was added and the mixture was heated at 80° C under stirring and dissolved. This solution was added to a mixture of 20ml of 10% gelatine solution and 2ml of 5% aqueous Alkanol B at 40° C. Then, this suspension liquid was applied to a colloidal mill five times. The remaining suspension liquid was washed out with 8ml of water and 2ml of 7% aqueous saponin solution from the mill and to the combined suspension liquid 10ml of silver chlorobromide emulsion was added, the resulting mixture was stirred for 2 minutes and allowed to stand at 40° C for 30 minutes. This emulsion was coated on the emulsion layer and the sensitive film was thus prepared.

On the other hand, on this film a gelatine solution containing 0.5g of tricetylmethylammonium bromide in 25ml of 10% gelatine solution was coated and a image receiving film was thus prepared. After exposure of the above sensitive film, the image receiving layer of the image receiving film was contacted with the above sensitive film and developed by the developer having the following composition:

| Composition of colour developer | |
| --- | --- |
| Sodium carbonate | 20.0g |
| Sodium hexametaphosphorate | 2.0g |
| Benzyl alcohol | 10.0g |
| 3-Acetamido-4-amino-N-N-diethylaniline | 2.0g |
| Water to | 1l |

The ph of the composition was adjusted to 11.0.

As the development inhibitor was released at the exposed part and this inhibitor diffused into the under fogged emulsion layer to control the development of the corresponding part in good condition. As a result, as the development at the under fogged emulsion layer was inhibited at the unexposed part, the coupling between the development principal agent and the coupler was caused to form a soluble magenta dye, which was transferred to imagewise the image receiving layer containing a mordant to form a clear positive magenta image.

EXAMPLE 4

On a cellulose triacetate base were coated the following succesively to obtain the sample (the weight is presented per 900cm$^2$):

1. red sensitive silver iodobromide emulsion containing 440mg of gelatine and 174mg of silver halide.

This emulsion contain 263mg of 1-hydroxy-4'-(4-tert-butylphenoxy)4-phenylazo-2-naphthanilide, 327mg of 1-hydroxy-N-[α-(2.4di-tertamylphenoxy)]butyl-2-naphtamide as coupler and further 7mg of exemplified compound (27).

2. an intermediate layer containing 83mg of gelatine and 5mg of dioctylhydroquinone 3. green sensitive silver iodobromide emulsion containing 400mg of gelatine and 243mg of silver halde This emulsion contains 24.5mg of 1-(2.4.6-trichlorophenyl)3-{3-[α-(2,4-di-tert-amylphenoxy)acetamido]-benzamido}-4-(4'-methoxyphenylazo)-5-pyrazolone, 24.3mg of 1-(2,4,6-trichlorophenyl)-3-{3-[α-2.4-di-tert-amylphenoxy)acetamido]benzamido}-5-pyrazolone as coupler and further 7mg of exemplifed compound (27). 8.7mg of dioctylhydroquinone was also contained a contamination inhibitor.

4. a gelatine intermediate layer containing 8.3mg of gelatine and 5mg of dioctylhydroquinone.

5. a green sensitive silver iodobromide emulsion containing 200mg of gelatine and 62mg of silver halide emulsion.

This emulsion contains 102.5mg of N-(p-benzoylacetamidobenzenesulfonyl)-N-(α-phenylprophyl)-p-toluidine as a coupler and further 2.3mg of dioctylhydroquinone as a contamination inhibitor.

As a control sample, a sample was prepared in the same way as described above except that the red and green sensitive layers do not contain the exemplified compound (27).

Both of the above samples were exposed through light wedge and developed at 24° C for 10 minutes by the following colour developer:

| Composition of colour developer | |
|---|---|
| Anhydrous sodium sulfate | 2.0g |
| N-ethyl-N-β-methanesulfonamidoethyl-3-methyl-4-aminoaniline sulfate | 5.0g |
| Sodium carbonate | 50.0g |
| Sodium bromide | 0.9g |
| Sodium hydroxide | 4.0g |
| Sodium hexametaphosphate | 0.5g |
| Benzyl alcohol | 4.0ml |
| Pure water to | 1l |

After development, the bleaching and fixing treatments were effected by an usual method.

The former sample containing the exemplifed compond (27) according to this invention was superior in sharpness and granularity to the control sample and furthermore exhibited little fog.

EXAMPLE 5

Samples A and B were prepared as follows
Sample A
In 30ml of ethyl acetate and 20ml of dibutyl phthalate 7.2g of exemplified compound (30) and 15g of 1-(2.4.6-trichlorophenyl)-3-{3-[(2.4-di-tert-amylphenoxy)acetamido]benzamido}-5-pyrozolone as magenta coupler were dissolved and the resulting solution was mixed with 20ml of 10% aqueous Alkanol B and 200ml of 5% aqueous gelatine soltuion and applied to a colloidal mill to emulsify and disperse. This dispersion liquid was added to 1 kg of green sensitive silver iodobromide emulsion and dispersed. This dispersed liquid was coated on a cellulose triacetate base and dried.

Sample B
Sample B was prepared in the same way as in ample A except that 7.2g of p-n-dodecyl-w-(1-phenyl-5-tetrazolylthio)acetophenone was used instead of exemplified compound (30).

After exposure, these samples A and B were treated in the same way as in Example 1. As a result, the γ value of the sample A is 0.40 and that of the sample B was 0.55. Therefore, as is clear from the above results, it is found that the usefulness of the development inhibitor releasing type compounds according to this invention is superior to that used in sample B.

Further, the compounds having the above formula according to this invention can promote sharpness and granularity even in cases where they are added to the photographic treating solution. Next, the exemplified sample will be illustrated by the following Reference.

Reference

An inner type colour photograpic film which is sold was exposed through light edge and developed at 20° C for 10 minutes by the colour developer having the following composition. After that, this film was bleached, fixed, washed, stabilized and dried in an usual way:

| Composition of colour developer | |
|---|---|
| N-ethyl-N-β-methanesulfonamidoethyl-3-methyl-4-aminoaniline sulfate | 5.0g |
| Sodium sulfite (anhydrous) | 2.0g |
| Benzyl alcohol | 3.8g |
| Sodium carbonate (monohydrate) | 50.0g |
| Potassium bromide | 1.0g |
| Potassium hydroxide | 0.55g |
| Exemplified compound (10) | 1.5g |
| Water to | 1l |

Also, as control, the same colour film was treated by the above same colour developer except that the exemplified compound (10) was not contained. As a result, the Reference according to this invention showed excellent image effect and extreme elevated sharpness and granularity in comparison with the control and its colour was bright.

What is claimed is:

1. A light-sensitive silver halide photographic material which comprises a compound forming a substantially colorless compound and releasing a development inhibitor by reacting with a oxidation product of a colour developing agent and having the following formula:

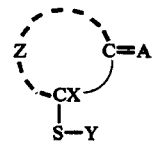

wherein A represents an oxygen atom or a $=NR_1$ radical in which $R_1$ is a hydroxyl or an amino radical that may be substituted, Z represents a non-metallic atomic group necessary to complete a 5-, 6- or 7-membered alicyclic or heterocyclic ring containing nitrogen, oxygen or sulfur, X represents a halogen atom, —O—W,

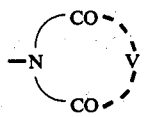

or -S-Y in which W represents an alkyl, aryl, heterocyclic ring, acyl or -SO$_2$R$_2$ radical wherein R$_2$ represents an alkyl, aryl or a heterocyclic ring radical, and V represents a non-metallic atomic group necessary to complete a heterocyclic ring containing nitrogen and Y represents a radical that forms a compound having development inhibiting action together with the sulfur atom when the —SY bond of the thioether is split.

2. A light-sensitive silver halide photographic materials as claimed in claim 1 in which Z represents a non-metallic atomic group necessary to complete a 5-, 6- or 7-membered alicyclic or heterocyclic ring containing an oxygen, nitrogen, or sulfur atom, each of which may be saturated or unsaturated and/or substituted with one or more of alkyl, aryl, alkoxyl, acyl, alkoxycarbonyl, halogen, nitrite, nitro, sulfonamido or acylamino or -S-Y radical and may form a condensed ring, V represents a non-metallic atomic group which together with

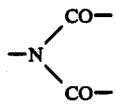

forms a heterocyclic ring selected from the group consisting of succinimide, phthalimide, hydantoin and urazol and Y represents a radical that forms a compound having development inhibiting action together with the sulfur atom when the —S-Y bond of the thioether is split, the compound being selected from the group consisting of an arylmercapto compound, a heterocyclic mercapto compound, a thioglycolic acid type compound, cysteine and glutathione.

3. A light-sensitive silver halide photographic material as claimed in claim 2 in which A represents an oxygen atom, and X represents a halogen atom.

4. A light-sensitive silver halide photographic material as claimed in claim 2 in which A represents =NR$_1$ in which R$_1$ is a hydroxyl or an amino radical that may be substituted, and X represents a halogen atom.

5. A light-sensitive silver halide photographic material as claimed in claim 2 in which Z represents an atom group selected from the group consisting of groups necessary to complete cyclopentanone, cyclohexanone, cyclohexadione, cyclohexenone, 2-, 3- and 4-piperidone, pyrrolidone, hydantoin, indanone, benzocyclohexenone, benzocycloheptenone and oxyindole.

6. A light-sensitive silver halide photographic material as claimed in Claim 2 wherein Y represents a radical that forms a compound having development inhibiting action, the compound being selected from the group consisting of 1-phenyl-2-mercaptotetrazole, 1-nitrophenyl-5-mercaptotetrazole, 1-naphthyl-5-mercaptotetrazole, 2-mercaptothiazole, 2-mercaptobenzthiazole, mercaptonaphthothiazole, mercapto-oxadiazole, mercaptopiperidine, 2-mercaptothiadiazolotriazine, mercaptotriazine, mercaptobenzene, 1-mercapto-2-benzoic acid, 1-mercapto2-nitrobenzoic acid, 1-mercapto-2-nitrobenzene, and 1-mercapto-3-heptadecanoyl-aminobenzene.

7. A light-sensitive silver halide photographic material of Claim 1, wherein the compound of the said formula is selected from the group consisting of (1)

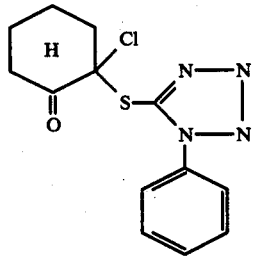

(2)

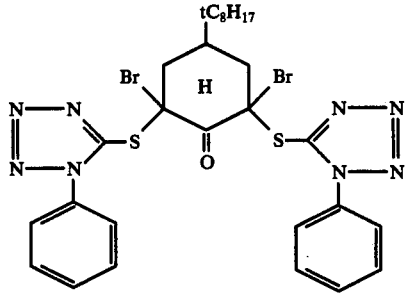

(3)

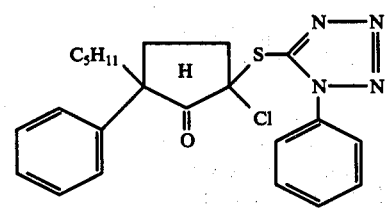

-continued
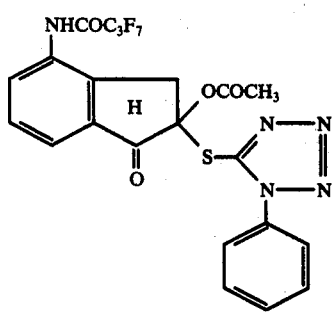 (4)
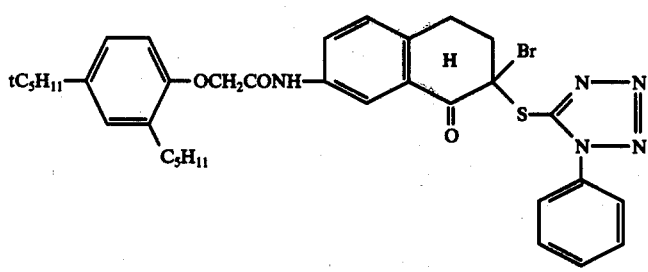 (5)
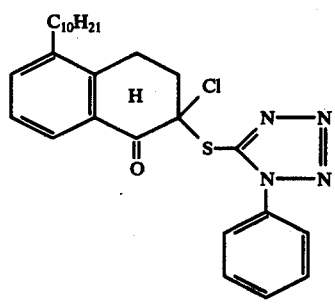 (6)
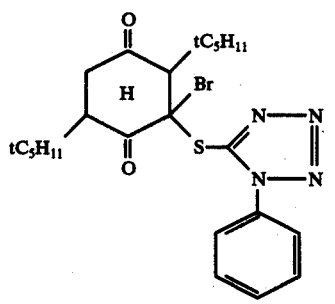 (7)
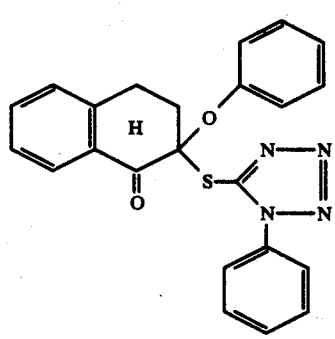 (8)
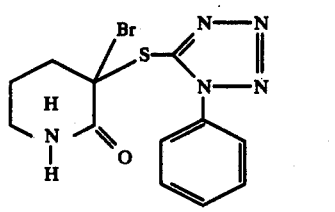 (9)

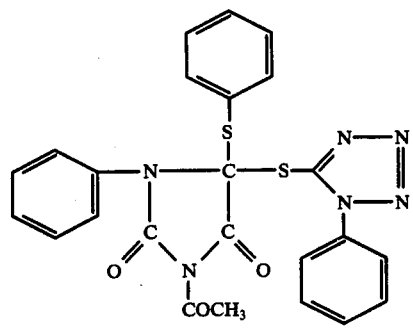
(10)
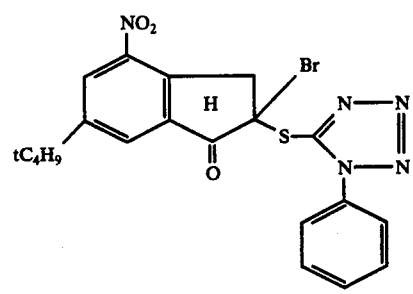
(11)
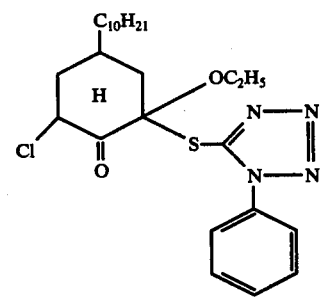
(12)
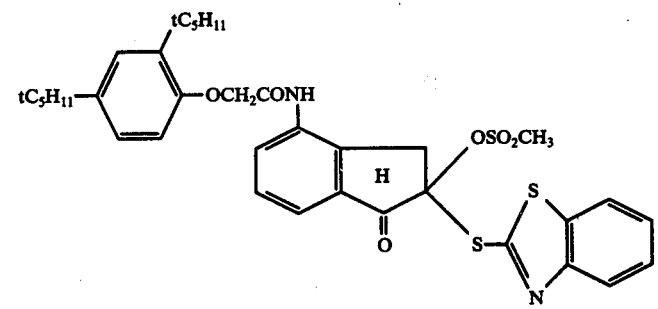
(13)
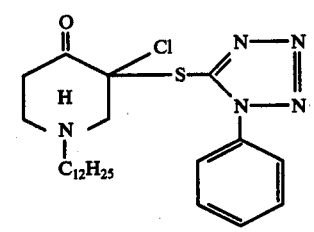
(14)

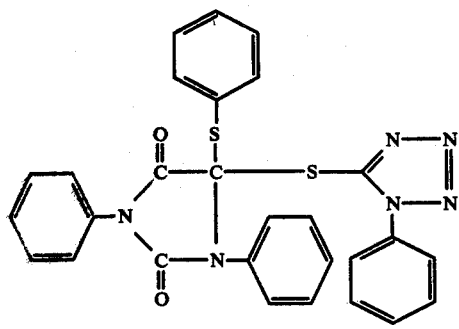
(15)
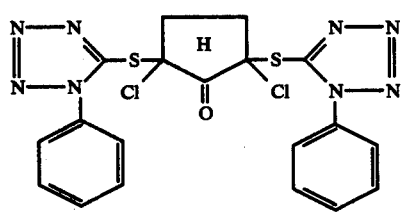
(16)
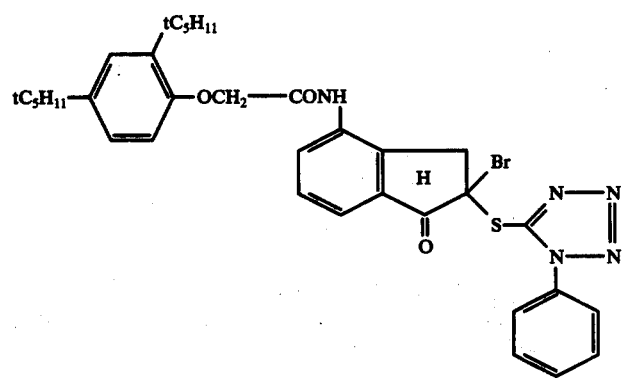
(17)
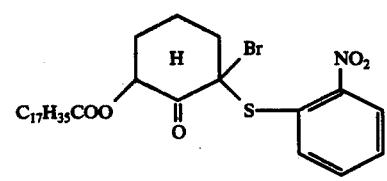
(18)
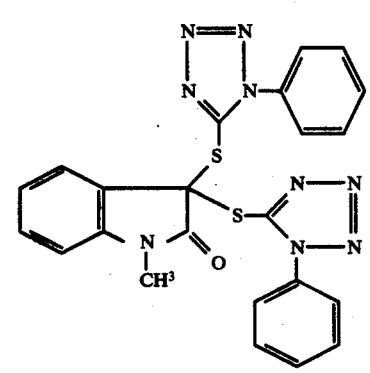
(19)

-continued
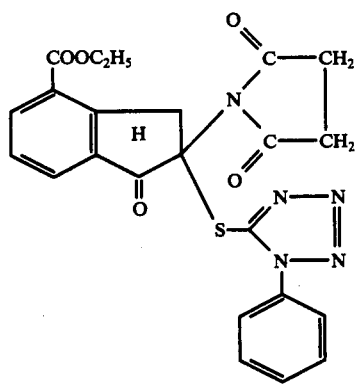 (20)
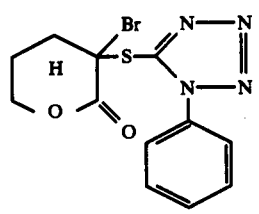 (21)
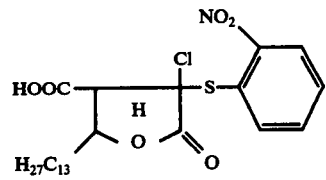 (22)
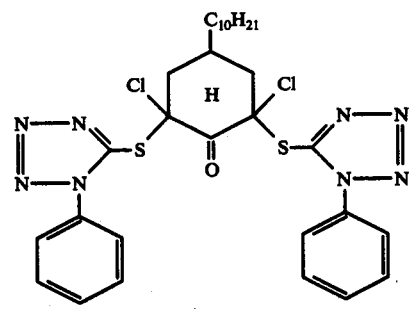 (23)
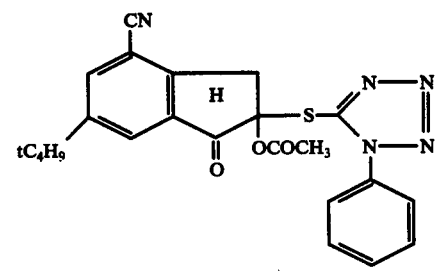 (24)
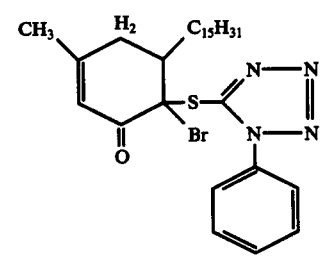 (25)

-continued
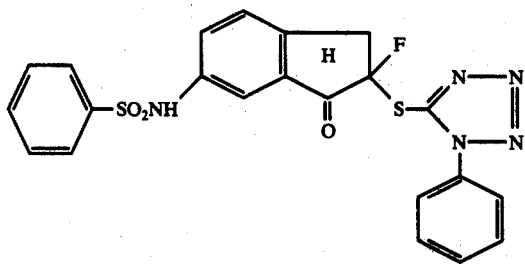
(26)
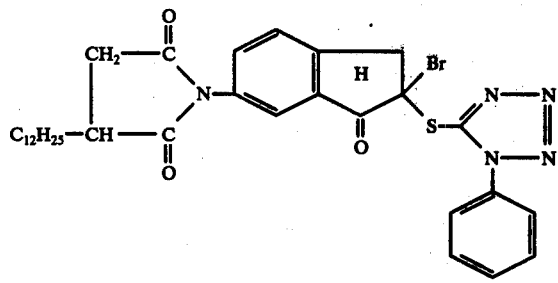
(27)
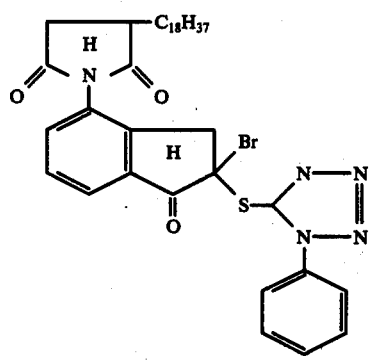
(28)
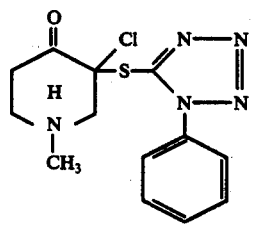
(29)
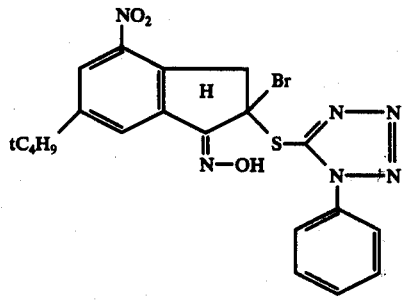
(30)
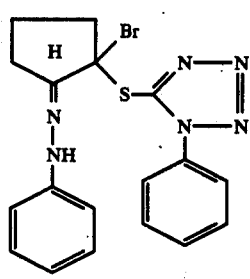
(31)

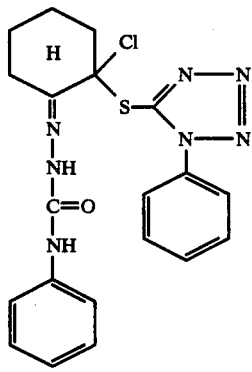

(32)

8. A process for developing an imagewise exposed light-sensitive silver halide photographic material comprising a compound forming a substantially colourless compound and releasing a development inhibitor by reacting with an oxidation product of a colour developing agent and having the following formula:

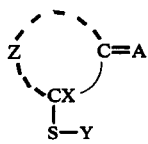

wherein A represents an oxygen atom or a $=NR_1$ radical in which $R_1$ is a hydroxyl or an amino radical that may be substituted, Z represents a non-metallic atomic group necessary to complete a 5-, 6- or 7-membered alicyclic ring or a heterocyclic ring containing nitrogen, oxygen or sulfur, X represents a halogen atom, —O—W,

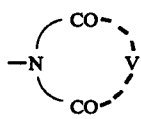

or -S-Y in which W represents an alkyl, aryl, heterocyclic ring, acyl or -$SO_2R_2$ radical wherein $R_2$ represents an alkyl, aryl or a heterocyclic ring radical, and V represents a non-metallic atomic group necessary to complete a heterocyclic ring containing nitrogen and Y represents a radical that forms a compound having development inhibiting action together with the sulfur atom when the —SY bond of the thioether is split which process comprises developing the exposed material with an alkaline developer containing a colour developing agent.

9. A process for developing a light-sensitive silver halide photographic material as claimed in claim 8 in which Z represents a non-metallic atomic group necessary to complete a 5-, 6- or 7-membered alicyclic or heterocyclic ring containing an oxygen, nitrogen, or sulfur atom, each of which may be saturated or unsaturated and/or substituted with one or more of alkyl, aryl, alkoxyl, acyl, alkoxylcarbonyl, halogen, nitrile, nitro, sulfonamide or acylamino or -S-Y radical and may form a condensed ring, V represents a non-metallic atomic group which together with

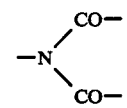

forms a heterocyclic ring selected from the group consisting of succinimide, phthalimide, hydantoin and urazol, and Y represents a radical that forms a compound having development inhibiting action together with the sulfur atom when the -S-Y bond of the thioether is split, the compound being selected from the group consisting of an arylmercapto compound, heterocyclic mercapto compound, thioglycolic acid type compound, cysteine and glutathione.

10. A process for developing a light-sensitive silver halide photographic material as claimed in claim 9 in which A represents an oxygen atom, and X represents a halogen atom.

11. A process for developing a light-sensitive silver halide photographic material as claimed in claim 9 in which A represents $=NR_1$ in which $R_1$ is a hydroxyl or an amino radical that may be substituted, and X represents a halogen atom.

12. A process for developing a light-sensitive silver halide photographic material as claimed in claim 9 in which Z represents an atom group selected from the group consisting of groups necessary to complete cyclopentanone, cyclohexanone, cyclohexadione, cyclohexenone, 2-, 3- and 4-piperidone, pyrollidone, hydantoin, indanone, benzocyclohexenone, benzocycloheptenone and oxyindole.

13. A process for developing a light-sensitive silver halide photographic material as claimed in claim 9 wherein Y represents a radical that forms a compound having development inhibiting action, the compound being selected from the group consisting of 1-phenyl2-mercaptotetrazole, 1-nitrophenyl-5-mercaptotetrazole, 2-mercaptothiazole, 2-mercaptobenzthiazole, mercaptonaphthothiazole, mercapto-oxadiazole, mercaptopiperidine, 2-mercaptothiadiazolotriazine, mercaptotriazine, mercaptobenzene, 1-mercapto-2-benzoic acid, 1-mercapto-2-nitrobenzoic, 1-mercapto-2-nitrobenzene, and 1-mercapto-3-heptadecanoylaminobenzene.

14. A process of Claim 8, wherein the compound of the said formula is selected from the group consisting of -continued
(23)
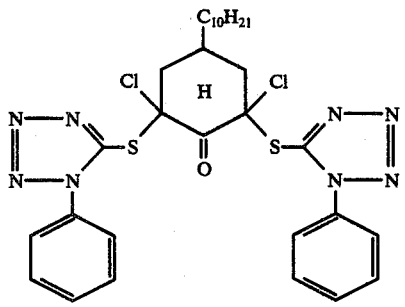
(24)
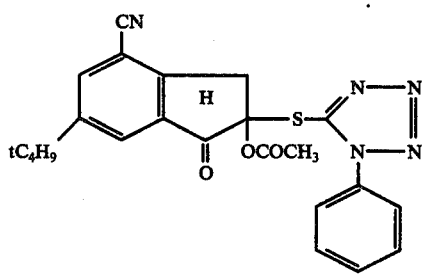
(25)
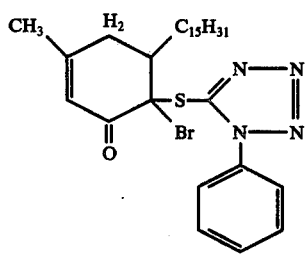
(26)
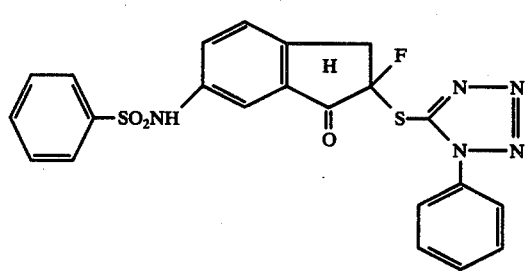
(27)
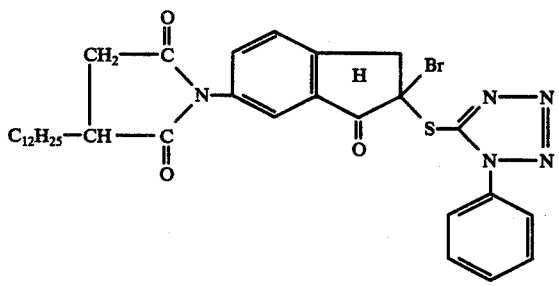
(28)
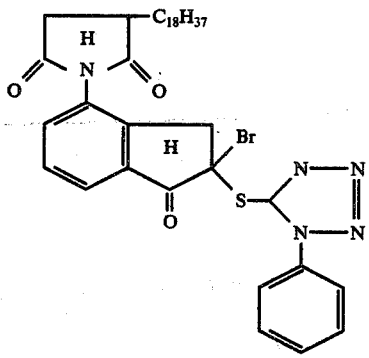

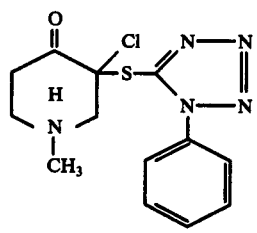
(29)
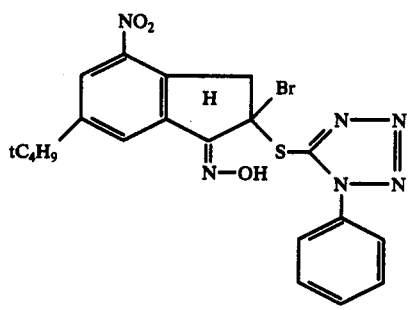
(30)
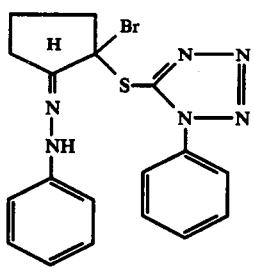
(31)
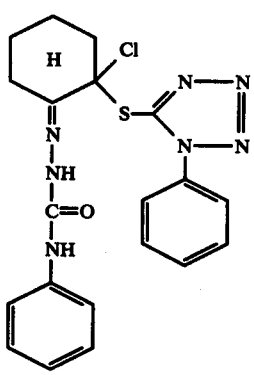
(32)
* * * * *

-continued
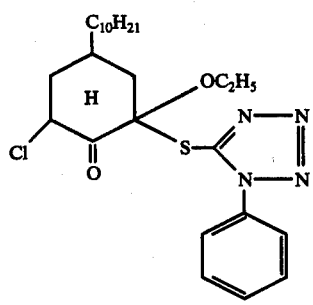 (12)
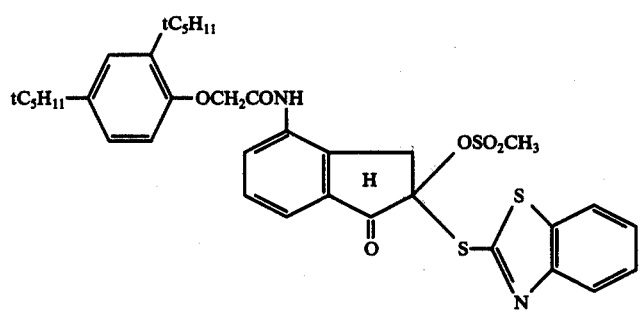 (13)
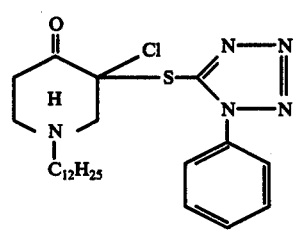 (14)
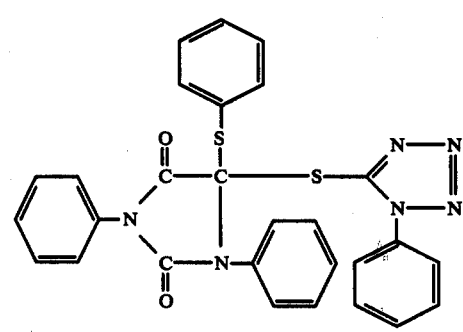 (15)
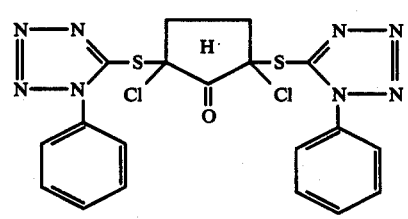 (16)

-continued
(17)
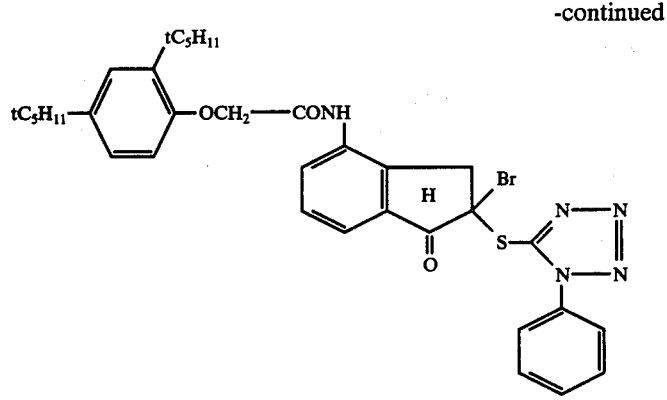
(18)
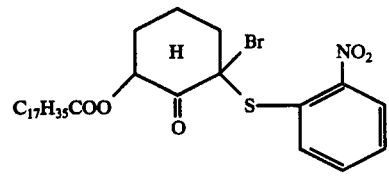
(19)
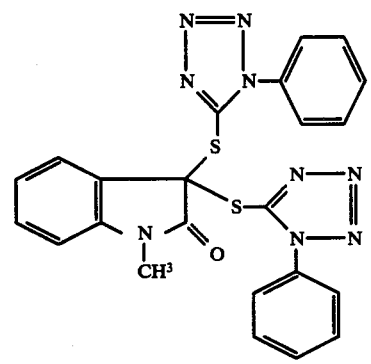
(20)
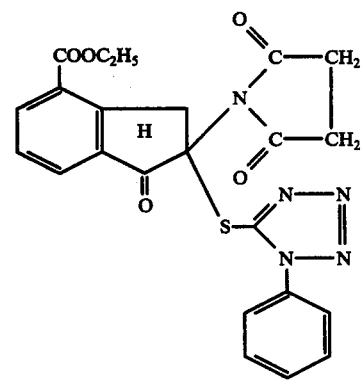
(21)
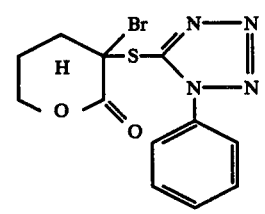
(22)
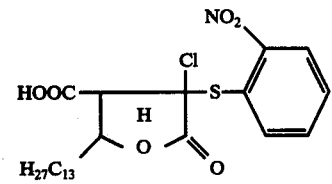

UNITED STATES PATENT AND TRADEMARK OFFICE
CERTIFICATE OF CORRECTION

PATENT NO. : 4,063,950
DATED : December 20, 1977
INVENTOR(S) : MITSUTO FUJIWHARA et al It is certified that error appears in the above—identified patent and that said Letters Patent are hereby corrected as shown below:

Column 1, line 24, and Column 2, line 47:

after "atom,", insert --- -O-W-, ---.

Signed and Sealed this

Twenty-fifth Day of September 1979

[SEAL]

Attest:

Attesting Officer

LUTRELLE F. PARKER
Acting Commissioner of Patents and Trademarks

UNITED STATES PATENT AND TRADEMARK OFFICE
CERTIFICATE OF CORRECTION

PATENT NO. : 4,063,950

DATED : December 20, 1977

INVENTOR(S) : MITSUTO FUJIWHARA et al

It is certified that error appears in the above-identified patent and that said Letters Patent are hereby corrected as shown below:

Column 1, line 24, and Column 2, line 47:

after "atom,", insert --- -O-W-, ---.

Signed and Sealed this

Twenty-fifth Day of September 1979

[SEAL]

Attest:

LUTRELLE F. PARKER

Attesting Officer     Acting Commissioner of Patents and Trademarks